(12) United States Patent
Maloney et al.

(10) Patent No.: US 11,834,491 B2
(45) Date of Patent: *Dec. 5, 2023

(54) ARGININE-FREE TNFR:FC-FUSION POLYPEPTIDE COMPOSITIONS

(71) Applicant: Biogen MA Inc., Cambridge, MA (US)

(72) Inventors: Kevin Maloney, Nashua, NH (US); Ke Gong, Lexington, MA (US); Roy Alston, Framingham, MA (US)

(73) Assignee: Biogen MA Inc., Cambridge, MA (US)

( * ) Notice: Subject to any disclaimer, the term of this patent is extended or adjusted under 35 U.S.C. 154(b) by 103 days.

This patent is subject to a terminal disclaimer.

(21) Appl. No.: 17/216,769

(22) Filed: Mar. 30, 2021

(65) Prior Publication Data

US 2021/0309719 A1    Oct. 7, 2021

Related U.S. Application Data

(63) Continuation of application No. 14/128,846, filed as application No. PCT/US2012/044988 on Jun. 29, 2012, now Pat. No. 10,995,130.

(60) Provisional application No. 61/504,110, filed on Jul. 1, 2011.

(51) Int. Cl.

| | | |
|---|---|---|
| *A61K 38/17* | (2006.01) | |
| *A61K 47/68* | (2017.01) | |
| *A61K 9/00* | (2006.01) | |
| *A61K 47/26* | (2006.01) | |
| *A61K 47/02* | (2006.01) | |
| *C07K 19/00* | (2006.01) | |
| *C07K 14/715* | (2006.01) | |
| *A61P 29/00* | (2006.01) | |
| *C07K 14/705* | (2006.01) | |
| *C07K 14/525* | (2006.01) | |
| *C07K 16/24* | (2006.01) | |

(52) U.S. Cl.
CPC ........ *C07K 14/7151* (2013.01); *A61K 9/0019* (2013.01); *A61K 38/1793* (2013.01); *A61K 47/26* (2013.01); *A61K 47/68* (2017.08); *C07K 19/00* (2013.01); *A61K 47/02* (2013.01); *A61P 29/00* (2018.01); *C07K 14/525* (2013.01); *C07K 14/70578* (2013.01); *C07K 16/241* (2013.01); *C07K 2319/30* (2013.01)

(58) Field of Classification Search
CPC ............... C07K 14/7151; C07K 19/00; C07K 2319/30; A61K 9/0019; A61K 38/1793; A61K 47/26; A61K 47/68
See application file for complete search history.

(56) References Cited

U.S. PATENT DOCUMENTS

| | | |
|---|---|---|
| 5,447,851 A | 9/1995 | Beutler et al. |
| 7,648,702 B2 | 1/2010 | Gombotz et al. |
| 10,995,130 B2 | 5/2021 | Maloney et al. |
| 2001/0021380 A1 | 9/2001 | Pluenneke |
| 2004/0220103 A1 | 11/2004 | Finck et al. |
| 2005/0164927 A1 | 7/2005 | Cheung et al. |
| 2007/0243185 A1 | 10/2007 | Gombotz et al. |
| 2008/0003220 A1 | 1/2008 | Gokarn |
| 2008/0254029 A1 | 10/2008 | Yanni et al. |
| 2010/0086559 A1 | 4/2010 | Gombotz et al. |
| 2014/0255400 A1 | 9/2014 | Maloney et al. |

FOREIGN PATENT DOCUMENTS

| | | |
|---|---|---|
| CN | 1612752 A | 5/2005 |
| CN | 1829739 A | 9/2006 |
| CN | 101217979 A | 7/2008 |
| JP | 2005-514394 A | 5/2005 |
| JP | 2005-527503 A | 9/2005 |
| JP | 2006-517233 A | 7/2006 |
| JP | 2006-519210 A | 8/2006 |
| JP | 2007-521315 A | 8/2007 |
| JP | 2008-515775 A | 5/2008 |
| JP | 2011-518110 A | 6/2011 |
| WO | WO 2000/62790 A2 | 10/2000 |
| WO | WO 2001/62272 A2 | 8/2001 |
| WO | WO 2003/053471 A1 | 7/2003 |
| WO | WO 2003/068260 A1 | 8/2003 |
| WO | WO 2003/072060 A2 | 9/2003 |
| WO | WO 2004/071439 A2 | 8/2004 |
| WO | WO 2004/075918 A1 | 9/2004 |
| WO | WO 2005/012353 A1 | 2/2005 |
| WO | WO 2006/020935 A2 | 2/2006 |
| WO | WO 2006/138181 A2 | 12/2006 |
| WO | WO 2008/051363 A2 | 5/2008 |
| WO | WO 2009/073569 A2 | 6/2009 |
| WO | WO 2012/013980 A1 | 2/2012 |

OTHER PUBLICATIONS

International Search Report and Written Opinion dated Oct. 16, 2012 for Application No. PCT/US2012/044988.
International Preliminary Report on Patentability dated Jan. 16, 2014 for Application No. PCT/US2012/044988.
[No Author Listed] Enbrel—Clinical Pharmacology. Health Central. Last accessed Apr. 8, 2011 via http://www.healthcentral.com/druglibrary/408/enbrel-clinical_pharmacology_pf.html. 10 pages.
[No Author Listed] Enbrel—Drug Description. Health Central. Last accessed Apr. 8, 2011 via http://www.healthcentral.com/druglibrary/408/enbrel_pf.html. 1 page.
[No Author Listed] Enbrel—Indication and Dosages. Health Central. Last accessed Apr. 8, 2011 via http://www.healthcentral.com/druglibrary/408/enbrel-indications_dosage_pf.html. 4 pages.
[No Author Listed] Phosphate-buffered Saline (PBS) Recipe, 2006 (Cold Spring Harbor Protocols. 1 page as printed; on-line at http://cshprotocols.cshlp.org/content/2006/1/pdb.rec8247).

(Continued)

*Primary Examiner* — Zachary C Howard
(74) *Attorney, Agent, or Firm* — Wolf, Greenfield & Sacks, P.C.

(57) ABSTRACT

Aspects of the invention are directed to arginine-free polypeptide-containing compositions and methods for treating disorders associated with inflammation or the autoimmune response. In particular, the polypeptide is etanercept.

18 Claims, No Drawings

(56) References Cited

OTHER PUBLICATIONS

Daans et al., Dynamic activation of bone morphogenetic protein signaling in collagen-induced arthritis supports their role in joint homeostasis and disease. Arthritis Res Ther. 2008; 10(5): R115. 10 pages.
Dore et al., The immunogenicity, safety, and efficacy of etanercept liquid administered once weekly in patients with rheumatoid arthritis. Clin Exp Rheumatol. 2007; 25(1): 40-6.
Lange et al., Suppression of protein aggregation by L-arginine. Curr Pharm Biotechnol. Jun. 2009;10(4):408-14.
Wang., Instability, stabilization, and formulation of liquid protein pharmaceuticals. Int J Pharm. Aug. 20, 1999;185(2):129-88.
Yanik et al., Etanercept IPS Protocol #0403, Version 5.0 dated Jun. 2, 2010, 73 pages, available at: https://web.emmes.com/study/bmt2/protocol/0403_protocol/0403_protocol.html.

ARGININE-FREE TNFR:FC-FUSION POLYPEPTIDE COMPOSITIONS

RELATED APPLICATIONS

This application is a continuation of U.S. patent application Ser. No. 14/128,846, filed Jun. 2, 2014, which is a national stage filing under 35 U.S.C. § 371 of International Application No. PCT/US2012/044988, filed Jun. 29, 2012, which claims the benefit under 35 U.S.C. § 119(e) of U.S. Provisional Patent Application No. 61/504,110, filed Jul. 1, 2011, the contents of each of which are hereby incorporated by reference in their entirety.

FIELD OF THE INVENTION

Certain aspects of the invention relates to therapeutic polypeptide-based compositions.

BACKGROUND

Therapeutic polypeptide preparations are often stored prior to use. Polypeptides, however, are unstable if stored in an aqueous form for extended periods of time, particularly in the absence of a stabilizing agent such as arginine. An alternative to relying on aqueous storage is to prepare a dry lyophilized form of a polypeptide, although, reconstitution of a dried polypeptide often results in aggregation or denaturation.

SUMMARY OF THE INVENTION

In some embodiments, arginine-free polypeptide compositions are provided. Formulations have been identified for preparing arginine-free polypeptide solutions that are stable for an extended period of time. These formulations have several benefits relative to arginine-stabilized solutions, including reduced cost and a reduced incidence of side-effects associated with the presence of arginine. Surprisingly, an aqueous polypeptide preparation can be stabilized by using a relatively high salt concentration in the absence of arginine or other stabilizing amino acid (e.g., lysine or glycine or other stabilizing amino acid, for example, one having a positive charge).

In some embodiments, provided herein are compositions comprising (or consisting, or consisting essentially of): an isolated polypeptide (e.g., a therapeutic polypeptide, for example that comprises an immunoglobulin domain); and salt in an amount sufficient to prevent aggregation of the polypeptide, thereby stabilizing the composition (e.g., in the absence of arginine or other added amino acid). In some embodiments, compositions provided herein are aqueous compositions (e.g., aqueous solutions). In some embodiments, the polypeptide and salt are provided in water without a buffer. In some embodiments, the composition comprises an aqueous buffer or other solvent (e.g., an organic solvent). In some embodiments, one or more excipients are included.

In some embodiments, aspects of the invention relate to arginine-free polypeptide compositions comprising an isolated polypeptide that includes an Fc region of a human immunoglobulin (e.g., IgG1). In some embodiments, aspects of the invention relate to arginine-free polypeptide compositions comprising an isolated polypeptide that includes an extracellular ligand-binding portion of a human p75 tumor necrosis factor (TNF). In some embodiments, aspects of the invention relate to arginine-free polypeptide compositions comprising an isolated polypeptide that is an extracellular ligand-binding portion of a human p75 tumor necrosis factor (TNF) receptor fused to the Fc region of a human IgG1.

In some aspects, provided herein are compositions comprising (or consisting, or consisting essentially of): an isolated polypeptide that is an extracellular ligand-binding portion of a human p75 tumor necrosis factor receptor fused to the Fc region of a human IgG1; and salt in an amount sufficient to prevent aggregation of the polypeptide, thereby stabilizing the composition (e.g., in the absence of arginine or other added amino acid). In some embodiments, compositions provided herein are aqueous compositions (e.g., aqueous solutions). In some embodiments, the protein and salt are provided in water without a buffer. In some embodiments, the composition comprises an aqueous buffer or other solvent (e.g., an organic solvent). In some embodiments, one or more excipients are included.

In other aspects, provided herein are methods comprising combining: an isolated polypeptide that is an extracellular ligand-binding portion of a human p75 tumor necrosis factor receptor fused to the Fc region of a human IgG1; aqueous buffer; and salt in an amount sufficient to prevent aggregation of the polypeptide, thereby formulating a stable composition.

In yet other aspects, provided herein are methods, comprising administering to an individual a composition, comprising: an isolated polypeptide that is an extracellular ligand-binding portion of a human p75 tumor necrosis factor receptor fused to the Fc region of a human IgG1; aqueous buffer; and salt in an amount sufficient to prevent aggregation of the isolated polypeptide, thereby stabilizing the composition.

In some embodiments, a composition contains less than 10 mM of free amino acids (e.g., arginine, lysine and/or glycine). In some embodiments, the composition contains less than 1 mM of free amino acids. In some embodiments, a composition contains less than 1 mM arginine. In some embodiments, a composition contains less than 0.5 mM arginine. In some embodiments, a composition contains less than 0.1 mM, less than 0.05 mM, less than 0.01 mM, less than 0.005 mM or less than 0.001 mM arginine. In some embodiments, the composition does not contain free amino acids. In some embodiments, the composition is substantially arginine-free. The isolated polypeptide of any one of the compositions described herein can comprise, as part of its amino acid sequence, arginine amino acid residues. Arginine residues that, together with other amino acid residues, form the amino acid sequence of a protein are not considered "free" amino acids. Thus, a composition that "does not contain amino acids" refers to a composition that does not contain free amino acids but can contain isolated polypeptide having arginine amino acid residues as part of is amino acid sequence.

In certain embodiments, compositions described herein comprise about 10 mg/ml to about 100 mg/ml of the isolated polypeptide. In some embodiments, the isolated polypeptide is etanercept.

In some embodiments, aqueous buffer is at a concentration of less than 100 mM, less than 50 mM, or less than 25 mM. In certain embodiments, the aqueous buffer is at a concentration of about 1 mM to about 15 mM. In some embodiments, the aqueous buffer is at a concentration of about 1 mM. In some embodiments, the aqueous buffer is at a concentration of less than 1 mM, less than 0.5 mM, less than 0.25 mM, less than 0.1 mM, less than 0.05 mM, or less than 0.01 mM. In some embodiments, the aqueous buffer is sodium phosphate, histidine, potassium phosphate, sodium or potassium citrate, maleic acid, ammonium acetate, tris-(hydroxymethyl)-aminomethane (tris), acetate, diethanolamine or a combination thereof. However, other buffers may be used (e.g., in low amounts) as aspects of the invention are not limited in this respect). In some embodiments, the compositions described herein do not contain an aqueous buffer. In such embodiments, the proteins in the composition are self-buffering, for example, moderately concentrated proteins can be self-buffering (e.g., in an aqueous solution without added buffer).

In some embodiments, salt is present at a concentration above 50 mM, or above 100 mM. In some embodiments, the salt is present at a concentration of about 120 mM to about 150 mM. In some embodiments, the salt is present at a concentration of greater than 150 mM, depending on the amount of aqueous buffer present in the solution. Generally, if the amount of aqueous buffer is reduced in the composition, the amount of salt (e.g., NaCl) is increased in order to preserve tonicity and thermal stability of the composition. For example, if aqueous buffer is present in a composition at a concentration of less than 15 mM, then the salt can be present in the composition at a concentration greater than 150 mM. In some embodiments, the salt is sodium chloride. The salt component of a composition refers to salt in addition to the salt present in aqueous buffer.

In other embodiments, any one of the compositions described herein can comprise an excipient. The excipient may be sucrose, lactose, glycerol, xylitol, sorbitol, Mannitol, maltose, inositol, trehalose, glucose, bovine serum albumin (BSA), human SA or recombinant HA, dextran, PVA, hydroxypropyl methylcellulose (HPMC), polyethyleneimine, gelatin, polyvinylpyrrolidone (PVP), hydroxyethylcellulose (HEC), polyethylene glycol, ethylene glycol, glycerol, dimethysulfoxide (DMSO), dimethylformamide (DMF), proline, L-serine, sodium glutamic acid, alanine, glycine, lysine hydrochloride, sarcosine, gamma-aminobutyric acid, TWEEN®-20 (polysorbate 20), TWEEN®-80 (polysorbate 80), SDS, polysorbate, polyoxyethylene copolymer, potassium phosphate, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, 2-O-beta-mannoglycerate or a combination thereof. Other excipients can be used, as aspects of the invention are not limited in this regard. In particular embodiments, the excipient is sucrose. In such embodiments, the sucrose may be at a concentration of from about 0.5% to about 1.5%. In certain embodiments, any of the compositions described herein may have a sucrose at a concentration of about 1% by weight.

In some embodiments, any of the compositions described herein can have a pH of about 5.5 to about 7.8. In some embodiments, any of the compositions described herein can have a pH of about 5.8 to about 6.5. In some embodiments, a composition described herein can have a pH of 5.8 to 6.5. In some embodiments, a composition can have a pH of 5.8, 5.9, 6.0, 6.1, 6.2, 6.3, 6.4, or 6.5.

In one embodiment, the composition comprises (or consists of, or consists essentially of) 50 mg/ml etanercept, about 10 mM sodium phosphate, about 140 mM sodium chloride, and about 1% sucrose, wherein the pH of the composition is about pH 6.0 to about pH 7.0.

In each of the embodiments described herein, the composition is free of additional L-arginine (arginine-free). That is, L-arginine is not added to or combined with the polypeptide in any of the compositions described herein. The polypeptide itself, however, can contain arginine amino acid residues, as described elsewhere herein.

Any of the compositions described herein may have a commercially-viable shelf life of at least 24 months.

Any of the compositions described herein may also be suitable for subcutaneous administration (e.g., non-toxic, purified, sterilized, and/or appropriate isotonicity).

In addition, in any of the compositions described herein, the isolated polypeptide may be purified.

In certain embodiments, compositions described herein may be sterilized.

Any of the compositions described herein may be used to treat rheumatoid arthritis, psoriatic arthritis, ankylosing spondylitis, Wegener's disease (granulomatosis), Crohn's disease (or inflammatory bowel disease), chronic obstructive pulmonary disease (COPD), Hepatitis C, endometriosis, asthma, cachexia, psoriasis, or atopic dermatitis, or other inflammatory or autoimmune-related illness, disorder, or condition. The compositions may be administered in an amount sufficient to treat (alleviate symptoms, halt or slow progression of) the disorder (e.g., a therapeutically effective amount).

DETAILED DESCRIPTION OF THE INVENTION

A commercially available soluble form of the TNF receptor fused to an Fc domain (TNFR:Fc) is known as etanercept. Etanercept (trade name ENBREL®) interferes with tumor necrosis factor (TNF) by acting as a TNF inhibitor. This dimeric fusion polypeptide consisting of the extracellular ligand-binding portion of the human 75 kilodalton (p75) tumor necrosis factor receptor (TNFR) linked to the Fc portion of human IgG1 is currently formulated with L-arginine to prevent aggregation of the polypeptide (See U.S. Pat. Nos. 5,447,851 and 7,648,702, incorporated herein by reference).

Arginine, while tolerated by most people, can cause serious side effects in some people. A severe allergic reaction, called anaphylaxis, can occur after arginine injections, as well as stomach discomfort, including nausea, stomach cramps, or an increased number of stools. Other potential side effects include low blood pressure and changes in numerous chemicals and electrolytes in the blood, such as high potassium, high chloride, low sodium, low phosphate, high blood urea nitrogen, and high creatinine levels. In theory, arginine may increase the risk of bleeding, increase blood sugar levels, increase potassium levels, and may worsen symptoms of sickle cell disease. Accordingly, individuals with liver or kidney disease, or those using coagulants are cautioned against using arginine.

As discussed in U.S. Pat. No. 6,748,702, aqueous compositions comprising Fc domain containing polypeptides are thought to require L-arginine in concentrations of about 1 mM to about 100 mM to prevent aggregation of the polypeptides. It is also believed to be necessary for long-term storage (e.g., two years or more) of such aqueous compositions.

Surprisingly, stable aqueous compositions (e.g., pharmaceutical compositions) that are substantially free of L-arginine (e.g., do not contain a substantial amount of L-arginine) can be prepared such that they are stable for a period of two years or more. Applicants have found that by increasing the concentration of salt and by decreasing the buffering capacity of the composition, it is still possible to provide a stable polypeptide composition, which can be administered subcutaneously to an individual. The term "stable" with respect to long-term storage is understood to mean that the active polypeptide of the pharmaceutical composition does not lose more than 20%, more than 15%, more than 10%, or more than 5% of its activity relative to activity of the composition at the beginning of storage.

In some embodiments, provided herein are compositions, comprising: an isolated polypeptide that is an extracellular ligand-binding portion of a human p75 tumor necrosis factor receptor fused to the Fc region of a human IgG1; aqueous buffer; and salt in an amount sufficient to prevent aggregation of the polypeptide, thereby stabilizing the composition, wherein the compositions comprise less than 1 mM concentrations of L-arginine. In certain other embodiments, the Fc containing polypeptide compositions are free or substantially free of L-arginine. "Substantially free," as used herein, refers to a composition without additional free amino acids, such as arginine. It is to be understood that the polypeptide itself may comprise the amino acid arginine in its structure. In some embodiments, a composition does not contain free arginine amino acids.

As used herein, the phrase "composition" or "compositions" may refer to a formulation(s) comprising a polypeptide prepared such that it is suitable for injection and/or administration into an individual in need thereof. A "composition" may also be referred to as a "pharmaceutical composition." In certain embodiments, the compositions provided herein are substantially sterile and do not contain any agents that are unduly toxic or infectious to the recipient. Further, as used herein, a solution or aqueous composition may mean a fluid (liquid) preparation that contains one or more chemical substances dissolved in a suitable solvent (e.g., water and/or other solvent, e.g., organic solvent) or mixture of mutually miscible solvents.

In addition, as used herein, the term "about" may mean that there can be variation in the concentration of a component of the described compositions that can be to 5%, 10%, 15% or up to and including 20% of the given value. For example, if a composition has about 10 mg/ml of an Fc domain containing polypeptide, that composition can have between 8 to 12 mg/ml of the stated polypeptide. In certain embodiments, the compositions comprise about 10 mg/ml to about 100 mg/ml of the polypeptide. In related embodiments, the compositions comprise 50 mg/ml or about 50 mg/ml of the polypeptide. Compositions may include more or less polypeptide as aspects of the invention are not limited in this respect.

In particular embodiments the Fc domain containing polypeptide is a soluble form of the TNF receptor fused to an Fc domain (TNFR:Fc). A commercially available TNFR:Fc is known as etanercept (ENBREL®, Immunex Corporation), which is a dimeric fusion polypeptide consisting of the extracellular ligand-binding portion of the human 75 kilodalton (p75) tumor necrosis factor receptor (TNFR) linked to the Fc portion of human IgG1. The Fc component of etanercept contains the constant heavy 2 (CH2) domain, the constant heavy 3 (CH3) domain and hinge region, but not the constant heavy 1 (CH1) domain of human IgG1. In some embodiments, an Fc domain can contain one of the domains described above, while in other embodiments, an Fc domain can contain all of the domains described above. Etanercept is produced by recombinant DNA technology in a Chinese hamster ovary (CHO) mammalian cell expression system. It consists of 934 amino acids and has an apparent molecular weight of/approximately 150 kilodaltons (Physicians' Desk Reference, 2002, Medical Economics Company Inc.).

Other polypeptides contemplated for use in particular compositions and methods described herein include without limitation recombinant fusion polypeptides comprising at least a portion of an Fc domain of an antibody. A polypeptide fused to an Fc domain and identical to or substantially similar to one of the following polypeptides is suitable for use in the present composition: a flt3 ligand, a CD40 ligand, erythropoietin, thrombopoeitin, calcitonin, Fas ligand, ligand for receptor activator of NF-kappa B (RANKL), tumor necrosis factor (TNF)-related apoptosis-inducing ligand (TRAIL), thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS).

In certain embodiments, the polypeptides include without limitation recombinant fusion polypeptides comprising an Fc domain of an antibody plus a receptor for any of the above-mentioned polypeptides or polypeptides substantially similar to such receptors. These receptors include without limitation: both forms of TNFR (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL (TRAIL receptors 1, 2, 3, and 4), and receptors that comprise death domains, such as Fas or Apoptosis-Inducing Receptor (AIR).

In other embodiments, the polypeptides include without limitation differentiation antigens (referred to as CD polypeptides) or their ligands or polypeptides substantially similar to either of these, which are fused to an Fc domain of an antibody. Such antigens are disclosed in Leukocyte Typing VI (Proceedings of the VI$^{th}$ International Workshop and Conference, Kishimoto, Kikutani et al., eds., Kobe, Japan, 1996). Similar CD polypeptides are disclosed in subsequent workshops. Examples of such antigens include CD27, CD30, CD39, CD40, and ligands thereto (CD27 ligand, CD30 ligand, etc.). Several of the CD antigens are members of the TNF receptor family, which also includes 41BB ligand and OX40. The ligands are often members of the TNF family, as are 41BB ligand and OX40 ligand. Accordingly, members of the TNF and TNFR families can be formulated as described herein.

In certain embodiments, enzymatically active polypeptides or their ligands may be used in the compositions and methods described herein. Examples include without limitation recombinant fusion polypeptides comprising an Fc domain of an antibody fused to all or part of one of the following polypeptides or their ligands or a polypeptide substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

In some embodiments, the compositions and methods described herein are used to prepare compositions comprising antibodies, human antibodies, humanized antibodies, chimeric antibodies, e.g., antibodies having human constant antibody immunoglobulin domains coupled to one or more murine variable antibody immunoglobulin domain, and/or non-human antibodies, or fragments thereof. Specific examples of antibodies suitable for use in the present compositions include without limitation commercially available antibodies such as muromonab-CD3 (Orthoclone OKT-3®, Ortho Biotech), abciximab (REOPRO®, Lilly), rituximab (RITUXAN®, IDEC), dacliximab (ZENAPAX®, Roche Laboratories), basiliximab (SIMULECT®, Novartis), infliximab (REMICADE®, Centocor), palivizumab (SYNAGIS®, MedImmune), trastuzumab (HERCEPTIN®, Genentech), gemtuzuman ozogamicin (MYLOTARG™, Wyeth-Ayerst), and alemtuzumab (CAMPATH®, Berlex). Currently each of the foregoing is available either as a lyophilized powder requiring rehydration or as a concentrate requiring dilution prior to administration. The present composition obviates the need for any manipulations prior to administration, e.g., rehydrating or dilution, while preserving stability of the active ingredients over long-term storage.

In particular embodiments, the compositions described herein are used to store polypeptides comprising an antibody conjugated to a cytotoxic or luminescent substance. Such substances include without limitation: maytansine derivatives (such as DM1); enterotoxins (such as a Staphylococcal enterotoxins); iodine isotopes (such as iodine-125); technetium isotopes (such as Tc-99m); cyanine fluorochromes (such as Cy5.5.18); and ribosome-inactivating polypeptides (such as bouganin, gelonin, or saporin-S6).

Examples of antibodies or antibody/cytotoxin or antibody/luminophore conjugates contemplated for use herein include without limitation those that recognize one or more of the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-4, IL-5, IL-8, IL-10, IL-2 receptor, IL-4 receptor, IL-6 receptor, IL-13 receptor, PDGF-β, VEGF, TGF, TGF-β2, TGF-β1, EGF receptor, VEGF receptor, C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of individuals with colon and/or pancreatic cancer, cancer-associated epitopes or polypeptides expressed on breast, colon, squamous cell, prostate, pancreatic, lung, and/or kidney cancer cells and/or on melanoma, glioma, or neuroblastoma cells, TRAIL receptors 1, 2, 3 and 4, the necrotic core of a tumor, integrin alpha 4 beta 7, the integrin VLA-4, B2 integrins, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human immunodeficiency virus (HIV), hepatitis B virus (HBV), *Streptococcus mutans*, and *Staphylococcus aureus*.

In some embodiments, the compositions described herein are used for anti-idiotypic antibodies, or substantially similar polypeptides, including without limitation anti-idiotypic antibodies against: an antibody targeted to the tumor antigen gp72; an antibody against the ganglioside GD3; or an antibody against the ganglioside GD2.

In other embodiments, the Fc domain containing polypeptide used in the compositions described herein are produced by living host cells that express the polypeptide, such as hybridomas in the case of antibodies, or host cells that that have been genetically engineered to produce the polypeptide in the case of fusion polypeptides or antibodies. Methods of genetically engineering cells to produce polypeptides are well known in the art. See, e.g., Ausubel et al., eds. (1990), Current Protocols in Molecular Biology (Wiley, New York). Such methods include introducing nucleic acids that encode and allow expression of the polypeptide into living host cells. These host cells can be without limitation bacterial cells, fungal cells, or animal cells grown in culture. Bacterial host cells include without limitation *Escherichia coli* cells. Examples of suitable *E. coli* strains include without limitation: HB101, DH5α, GM2929, JM109, KW251, NM538, NM539, and any *E. coli* strain that fails to cleave foreign DNA. Fungal host cells that can be used include without limitation *Saccharomyces cerevisiae, Pichia pastoris* and *Aspergillus* cells. A few examples of animal cell lines that can be used are CHO, VERO, BHK, HeLa, Cos, MDCK, 293, 3T3, and W138. New animal cell lines can be established using methods well know. by those skilled in the art (e.g., by transformation, viral infection, and/or selection). Optionally, the polypeptide can be secreted by the host cells into the medium.

In certain embodiments, the expressed Fc domain containing polypeptide are purified by any standard method. When the Fc domain containing polypeptide is produced intracellularly, the particulate debris is removed, for example, by centrifugation or ultrafiltration. When the polypeptide is secreted into the medium, supernatants from such expression systems can be first concentrated using standard polypeptide concentration filters. Protease inhibitors can also be added to inhibit proteolysis and antibiotics can be included to prevent the growth of microorganisms.

In some embodiments, the Fc domain containing polypeptide are purified using, for example, hydroxyapatite chromatography, gel electrophoresis, dialysis, and affinity chromatography, and/or any combination of purification techniques known or yet to discovered. For example, protein A can be used to purify Fc domain containing polypeptides that are based on human gamma 1, gamma 2, or gamma 4 heavy chains (Lindmark et al., 1983, J. Immunol. Meth. 62:1-13). Protein G is recommended for all mouse isotypes and for human gamma 3 (Guss et al., 1986, EMBO J. 5:1567-1575).

Other techniques for polypeptide purification such as fractionation on an ion-exchange column, ethanol precipitation, reverse phase HPLC, chromatography on silica, chromatography on heparin SEPHAROSE™ (a crosslinked, beaded-form of agarose), chromatography on an anion or cation exchange resin (such as a polyaspartic acid column), chromatofocusing, SDS-PAGE, and ammonium sulfate precipitation can also be utilized depending on need. Other polypeptide purification techniques/methods can be used.

In particular embodiments, the compositions described herein are prepared by combining, in addition to a purified polypeptide described above, buffer, salt (e.g., NaCl), and an additional excipient (e.g., sucrose). In some embodiments, the present compositions comprise less than 1 mM L-arginine, while in other embodiments, the compositions described herein are free or substantially free of arginine (e.g., L-arginine). It will be understood one of ordinary skill in the art that the combining of the various components to be included in the composition can be done in any appropriate order, namely, the buffer can be added first, middle or last and the tonicity modifier can also be added first, middle or last. It is also to be understood by one of ordinary skill in the art that some of these chemicals can be incompatible in certain combinations, and accordingly, are easily substituted with different chemicals that have similar properties but are compatible in the relevant mixture.

Aggregation inhibitors reduce a polypeptide's tendency to associate in inappropriate or unwanted ternary or quaternary complexes. Surprisingly, the present inventors have found that by increasing the salt and by decreasing the buffer capacity in a composition comprising an Fc containing polypeptide, there is no need for the addition of free amino acids (e.g., arginine, lysine, glycine). The polypeptides within the arginine-free compositions remain active (effective) and can be stored for at least 24 months. In certain embodiments, the salt concentration is greater than 100 mM, while in other embodiments, the salt concentration is about 140 mM, or greater. Salts, used herein, can include without limitation sodium chloride (NaCl), potassium chloride (KCl), sodium citrate ($Na_3C_6H_5O_7.2H_2O$), magnesium sulphate ($MGSO_4$), calcium chloride (CaCl), sodium hypochlorite (NaClO), sodium nitrate ($NaNO_3$), mercury sulphide (HgS), sodium chromate ($Na_2CrO_4$) and magnesium dioxide ($MgO_2$). Salt both maintains the isotonicity and the thermal stability of the composition, for example, in the absence of arginine (e.g., L-arginine).

Buffering agents maintain pH in a desired range and various buffers suitable for use in the compositions described herein include without limitation histidine, potassium phosphate, sodium or potassium citrate, maleic acid, ammonium acetate, tris-(hydroxymethyl)-aminomethane (tris), various forms of acetate and diethanolamine. In certain embodiments, the buffer is sodium phosphate as its buffering capacity is at or near pH 6.2. In some embodiments, the concentration of the buffer in the compositions is about 25 mM, or less. In some embodiments, the concentration of the buffer is 25 mM. In particular embodiments, the concentration of the buffer is about 10 mM, or less. In some embodiments, the concentration of the buffer is 10 mM. Buffers are well known in the art and are manufactured by known methods and available from commercial suppliers.

When the pH of the composition is set at or near physiological levels, comfort of the individual upon administration is maximized. In certain embodiments, the pH is about 5.8 to 8.4. In other embodiments, the pH is with about 6.2 to 7.4. It is to be understood that the pH can be adjusted as necessary to maximize stability and solubility of the polypeptide in a particular composition and as such, a pH outside of physiological ranges, yet tolerable to the individual, is within the scope of the invention.

In certain embodiments, excipients, also referred to as chemical additives, co-solutes, or co-solvents, that stabilize the polypeptide while in solution (also in dried or frozen forms) are added to a composition. Examples include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols, (e.g., PEG, ethylene glycol and glycerol) dimethysulfoxide (DMSO) and dimethylformamide (DMF); amino acids such as: proline, L-serine, sodium glutamic acid, al nine, glycine, lysine hydrochloride, sarcosine and gamma-aminobutyric acid; surfactants such as: TWEEN-80™ (polysorbate 80), TWEEN-20Ω (polysorbate 20), SDS, polysorbate, polyoxyethylene copolymer; and miscellaneous excipients such as: potassium phosphate, sodium acetate, ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate or any combination of the above.

In certain embodiments, the concentration of one or more excipients in a composition described herein is/are about 0.001 to 5 weight percent, while in other embodiments, the concentration of one or more excipients is/are about 0.1 to 2 weight percent. Excipients are well known in the art and are manufactured by known methods and available from commercial suppliers. In some embodiments, the excipient is sucrose. In other embodiments, sucrose is present in the composition at a concentration of about 1 percent.

In a particular embodiment, a composition described herein comprises (or consists of, or consists essentially of) about 25 to about 50 mg TNFR:Fc (e.g., etanercept), about 10 mM to about 50 mM sodium phosphate (e.g., monobasic and/or dibasic), about 0.75% to about 1.25% sucrose, about 50 mM to about 150 mM NaCl, at about pH 6.0 to about pH 7.0.

In another embodiment, a composition described herein comprises (or consists of, or consists essentially of) about 50 mg/ml TNFR:Fc, about 10 mM sodium phosphate, about 140 mM sodium chloride, and about 1% sucrose at about pH 6.2.

In certain embodiments, provided herein are methods of treating an individual comprising administering to the individual a therapeutically effective amount of the composition described herein, wherein the individual has a disease or disorder that can be beneficially treated with a Fc domain containing polypeptide in the composition. In some embodiments, the Fc domain containing polypeptide is derived from the same species of individual as is to be treated with the composition. In particular embodiments, the individual is a human in need of treatment. When the Fc domain containing polypeptide of the composition is TNFR:Fc, examples of diseases or disorders that can be treated include but are not limited to rheumatoid arthritis, psoriatic arthritis, ankylosing spondylitis, Wegener's disease (granulomatosis), Crohn's disease (or inflammatory bowel disease), chronic obstructive pulmonary disease (COPD), Hepatitis C, endometriosis, asthma, cachexia, psoriasis, and atopic dermatitis. Additional diseases or disorders that can be treated with TNFR:Fc include those described in WO 00/62790, WO 01/62272 and U.S. Patent Application No. 2001/0021380.

In other aspects, provided herein are polypeptide compositions having improved long-term storage such that the active ingredient, e.g., an Fc domain containing polypeptide, is stable over the course of storage in liquid (or frozen) states. As used herein, the phrase "long-term" storage is understood to mean that the composition can be stored for three months or more, for six months or more, or for one year, or two years, or more. Long term storage is also understood to mean that the composition is stored either as a liquid at 2-8° C. or is frozen, e.g., at −20° C. or colder. In certain embodiments, the composition can be frozen and thawed more than once. The term "stable" with respect to long-term storage is understood to mean that the active polypeptide of the composition does not lose more than 20%, or 15%, or even 10% of its activity. In particular embodiments, the active polypeptide of the composition does not lose more than 5% of its activity relative to activity of the composition at the beginning of storage. Stability of a composition can be assessed based on potency, appearance, concentration, pH, and oxidation, and can be assessed using, for example, hydrophobic interaction chromatography (HIC), capillary electrophoresis-sodium dodecyl sulfate (CE-SDS), high accuracy (HIAC) liquid particle counters, and/or isoelectric focusing. Other protein stability assays are known in the art and can be used herein.

The appropriate dosage, or therapeutically effective amount, of the Fc domain-containing polypeptide of the compositions will depend on the condition to be treated, the severity of the condition, prior therapy, and the individual's clinical history and response to the therapeutic agent. The proper dose can be adjusted according to the judgment of the attending physician such that it can be administered to the individual one time or over a series of administrations. The composition can be administered as a sole therapeutic or in combination with additional therapies as needed.

In certain embodiments, the effective Fc domain containing polypeptide amount per adult dose ranges from about 1-500 mg/m$^2$, or from about 1-200 mg/m$^2$, or from about 1-40 mg/m$^2$ or about 5-25 mg/m$^2$. Alternatively, a flat dose may be administered, whose amount may range from 2-500 mg/dose, 2-100 mg/dose or from about 10-80 mg/dose. If the dose is to be administered more than one time per week, an exemplary dose range is the same as the foregoing described dose ranges or lower and preferably administered two or more times per week at a per dose range of 25-100 mg/dose. In other embodiments, an acceptable dose for administration by injection contains 80-100 mg/dose, or alternatively, contains 80 mg/dose. The dose can be administered at biweekly, weekly doses, or separated by several weeks (for example 2 to 8). In a particular embodiment, TNFR:Fc (etanercept) is administered at 25 mg by a single subcutaneous (SC) injection. Other routes of administration are contemplated.

In many instances, an improvement in an individual's condition will be obtained by a dose of up to about 100 mg of the composition one to three times per week over a period of at least three weeks, though treatment for longer periods may be necessary to induce the desired degree of improvement. For incurable chronic conditions the regimen may be continued indefinitely. For pediatric individuals (ages 4-17), a suitable regimen involves a dose of 0.4 mg/kg to 5 mg/kg of a the polypeptides of the invention, administered one or more times per week.

In other embodiments, the compositions described herein are prepared in a bulk formulation and as such, the components of the composition are adjusted so that it is higher than would be required for administration and diluted appropriately prior to administration.

In certain embodiments, the compositions described herein are administered parenterally, e.g., subcutaneously, intramuscularly, intravenously, intraperitoneal, intracerebrospinal, intra-articular, intrasynovial, and/or intrathecal. Parenteral administration can be by bolus injection or continuous infusion. compositions for injection may be presented in unit dosage form, e.g., in ampoules or in multi-dose containers, with an added preservative. In addition, a number of recent drug delivery approaches have been developed and the compositions of the present invention are suitable for administration using these new methods, e.g., INJECT-EASE™ (automatic injector), GENJECT™ (injection device), injector pens such as GENPEN™, and needleless devices such as MEDIJECTOR™ and BIOJECTOR™. The present composition can also be adapted for yet to be discovered administration methods. See also Langer, 1990, Science, 249:1527-1533.

In some embodiments, the compositions described herein are formulated as a depot preparation. Such long acting compositions may be administered by implantation (for example subcutaneously or intramuscularly) or by intramuscular injection. Thus, for example, the compositions may be modified with suitable polymeric or hydrophobic materials (for example as an emulsion in an acceptable oil) or ion exchange resins, or as sparingly soluble derivatives, for example, as a sparingly soluble salt.

In other embodiments, the compositions described herein are presented in a vial, pack or dispenser device which may contain one or more unit dosage forms containing the active ingredient. In some embodiments, the dispenser device comprises a syringe having a single dose of the liquid composition ready for injection. The syringe can be accompanied by instructions for administration.

In other aspects, provided herein are kits or containers, which contain an aqueous composition of the invention. The concentration of the polypeptide in the aqueous composition can vary over a wide range. In certain embodiments, it ranges of from about 0.05 to about 20,000 micrograms per milliliter (μg/ml) of aqueous composition. The kit can also be accompanied by instructions for use.

The compositions are further described below by way of non-limiting examples.

EXAMPLES

Example 1: One Embodiment of a Stable Polypeptide Composition

TABLE 1

Etanercept composition.

| Ingredient | Function | Amount per mL of the dosage form | | Grade |
|---|---|---|---|---|
| Etanercept | Active ingredient | 50 mg | | N/A |
| Sodium phosphate, dibasic, heptahydrate | Buffer | 0.67 mg | 10 mM | USP |
| Sodium phosphate, monobasic, monohydrate | Buffer | 1.04 mg | | USP |
| Sodium chloride (NaCl) | Stabilizer | 8.18 mg | 140 mM | USP/Ph.Eur. |
| Sucrose | Stabilizer | 0.01 mg | 1% | NF/Ph.Eur. |
| Water (for injection) | Solvent | Q.S. | | USP/Ph.Eur. |

Example 2: Stability Data for the Polypeptide Composition at −70° C.

TABLE 2

Stability Data for Etanercept at −70° C.

| Test Method | Expected Result/Range | Time Points (Months) | | | |
|---|---|---|---|---|---|
| | | Initial | 1 | 3 | 6 |
| Appearance | Color < Y3, Clarity < 80NTU, Report (FIO) visible particles | Y7-Y6 3-6NTU | Y7-Y6 0-3NTU | Y7-Y6 3-6NTU | Y7-Y6 3-6NTU |

TABLE 2-continued

Stability Data for Etanercept at −70° C.

| Test Method | Expected Result/Range | Time Points (Months) | | | |
|---|---|---|---|---|---|
| | | Initial | 1 | 3 | 6 |
| Protein Concentration By UV | 45.0 to 55.0 mg/mL | 48.2 | 49.4 | 51.5 | 51.0 |
| Size Exclusion Chromatography (SEC) | Report % HMW, expected result is ≤5.0% HMW | 1.2 | 1.1 | 1.1 | 1.2 |

Example 3: Stability Data for the Polypeptide Composition at 5±3° C.

TABLE 3

Stability Data for Etanercept at 5 ± 3° C.

| Test Method | Expected Result/Range | Time Points (Months) | | | |
|---|---|---|---|---|---|
| | | Initial | 1 | 3 | 6 |
| Appearance | Color < Y3, Clarity < 80NTU, Report (FIO) visible particles | W-Y7 3-6NTU Particle | Y7-Y6 W-3NTU Particle | Y7-Y6 6-18NTU Particle | Y7-Y6 3-6NTU Particle |
| Protein Conc. By UV | 45.0 to 55.0 mg/mL | 47.8 | 49.3 | 51.3 | 50.0 |
| Size Exclusion Chromatography (SEC) | Report % HMW, expected result is ≤5.0% HMW | 1.2 | 1.3 | 1.3 | 1.6 |
| Particulate | Report result ≥10 μm | 460 | 435 | 135 | 180 |
| | Report result ≥25 μm | 110 | 25 | 55 | 25 |

EQUIVALENTS AND SCOPE

Those skilled in the art will recognize or be able to ascertain using no more than routine experimentation many equivalents to the specific embodiments described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, up to 10%, up to 5%, or up to 1% of a given value. Alternatively, the term can mean within an order of magnitude, for example, within 5-fold, or within 2-fold, of a value. Where particular values are described in the application and claims, unless otherwise stated the term "about" meaning within an acceptable error range for the particular value should be assumed.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the methods of the invention can be excluded from any one or more claims, for any reason, whether or not related to the existence of prior art.

What is claimed is:

1. A syringe comprising a composition, wherein the composition comprises:
    an isolated polypeptide that is an extracellular ligand-binding portion of a human p75 tumor necrosis factor receptor fused to the Fc region of a human IgG1 at a concentration of 10 mg/mL to 100 mg/mL;
    aqueous buffer at a concentration of less than 25 mM, wherein the aqueous buffer is sodium phosphate, potassium phosphate, sodium or potassium citrate, maleic acid, ammonium acetate, tris-(hydroxymethyl)-aminomethane (tris), acetate, diethanolamine, or a combination thereof;
    salt at a concentration of greater than 100 mM; and
    a sugar,
    wherein the composition does not contain free amino acids.

2. The syringe of claim 1, wherein the isolated polypeptide is etanercept.

3. The syringe of claim 1, wherein the aqueous buffer is present at a concentration of 1 mM to 15 mM.

4. The syringe of claim 1, wherein the pH of the composition is 5.5 to 7.8.

5. The syringe of claim 1, wherein the salt is present at a concentration of 120 mM to 150 mM.

6. The syringe of claim 1, wherein the salt is sodium chloride, potassium chloride, calcium chloride, sodium citrate, magnesium sulfate, or a combination thereof.

7. The syringe of claim 6, wherein the salt is sodium chloride.

8. The syringe of claim 1, wherein the sugar is present at a concentration of 0.1% to 2.0%.

9. The syringe of claim 1, wherein the sugar is sucrose, lactose, xylitol, sorbitol, mannitol, maltose, inositol, trehalose, glucose, or a combination thereof.

10. The syringe of claim 9, wherein the sugar is sucrose.

11. The syringe of claim 10, wherein the sucrose is present at a concentration of 0.5% to 1.5%.

12. A kit comprising the syringe of claim 1.

13. A syringe comprising a composition, wherein the composition comprises:
    an isolated polypeptide that is an extracellular ligand-binding portion of a human p75 tumor necrosis factor receptor fused to the Fc region of a human IgG1 at a concentration of 10 mg/mL to 100 mg/mL;
    aqueous buffer at a concentration of 1 mM to 15 mM, wherein the aqueous buffer is sodium phosphate, potassium phosphate, sodium or potassium citrate, maleic acid, ammonium acetate, tris-(hydroxymethyl)-aminomethane (tris), acetate, diethanolamine, or a combination thereof;
    salt at a concentration of 120 mM to 150 mM; and
    sucrose at a concentration of 0.5% to 1.5%,
    wherein the pH of the composition is 5.5 to 7.8,
    wherein the composition does not contain free amino acids.

14. The syringe of claim 13, wherein the composition comprises:
    etanercept at a concentration of 50 mg/mL;
    sodium phosphate at a concentration of 10 mM;
    sodium chloride at a concentration of 140 mM; and
    sucrose at a concentration of 1%,
    wherein the pH of the composition is 5.8 to 6.5.

15. A kit comprising the syringe of claim 13.

16. A kit comprising:
    a syringe; and
    a vial containing a composition, wherein the composition comprises:
        an isolated polypeptide that is an extracellular ligand-binding portion of a human p75 tumor necrosis factor receptor fused to the Fc region of a human IgG1 at a concentration of 10 mg/mL to 100 mg/mL;
        aqueous buffer at a concentration of less than 25 mM, wherein the aqueous buffer is sodium phosphate, potassium phosphate, sodium or potassium citrate, maleic acid, ammonium acetate, tris-(hydroxymethyl)-aminomethane (tris), acetate, diethanolamine, or a combination thereof;
        salt at a concentration of greater than 100 mM; and
        a sugar,
        wherein the composition does not contain free amino acids.

17. The kit of claim 16, wherein the composition comprises:
    etanercept at a concentration of 10 mg/mL to 100 mg/mL;
    aqueous buffer at a concentration of 1 mM to 15 mM;
    salt at a concentration of 120 mM to 150 mM; and
    sucrose at a concentration of 0.5% to 1.5%,
    wherein the pH of the composition is 5.5 to 7.8.

18. The kit of claim 16, wherein the composition comprises:
    etanercept at a concentration of 50 mg/mL;
    sodium phosphate at a concentration of 10 mM;
    sodium chloride at a concentration of 140 mM; and
    sucrose at a concentration of 1%,
    wherein the pH of the composition is 5.8 to 6.5.

* * * * *